(12) United States Patent
Nelson et al.

(10) Patent No.: US 11,433,181 B2
(45) Date of Patent: Sep. 6, 2022

(54) VARIABLE FLOW RATE CONTROL DEVICE

(71) Applicant: Avent, Inc., Alpharetta, GA (US)

(72) Inventors: Christopher S. Nelson, Cork (IR); Andrew Schaffer, Costa Mesa, CA (US); Mark D. Mendillo, Mission Viejo, CA (US)

(73) Assignee: Avent, Inc., Alpharetta, GA (US)

( * ) Notice: Subject to any disclaimer, the term of this patent is extended or adjusted under 35 U.S.C. 154(b) by 71 days.

(21) Appl. No.: 15/754,095

(22) PCT Filed: Aug. 27, 2015

(86) PCT No.: PCT/US2015/047145
§ 371 (c)(1),
(2) Date: Feb. 21, 2018

(87) PCT Pub. No.: WO2017/034568
PCT Pub. Date: Mar. 2, 2017

(65) Prior Publication Data
US 2019/0009021 A1   Jan. 10, 2019

(51) Int. Cl.
*A61M 5/168* (2006.01)
*F16K 7/10* (2006.01)
(Continued)

(52) U.S. Cl.
CPC .... *A61M 5/16813* (2013.01); *A61M 5/16881* (2013.01); *A61M 5/16886* (2013.01);
(Continued)

(58) Field of Classification Search
CPC .......... A61M 5/16813; A61M 5/16804; A61M 5/16881; A61M 2005/1405;
(Continued)

(56) References Cited

U.S. PATENT DOCUMENTS

| | | | | |
|---|---|---|---|---|
| 401,950 A | * | 4/1889 | Haussmann | ........ A61M 5/2425 604/214 |
| 2,750,959 A | * | 6/1956 | Von Seggern | ............ F16K 7/07 251/5 |

(Continued)

FOREIGN PATENT DOCUMENTS

| | | |
|---|---|---|
| DE | 19508129 A1 | 9/1996 |
| EP | 1 703 182 A1 | 9/2006 |

(Continued)

OTHER PUBLICATIONS

Kay Wessin, "Thickness Measurements on Balloon Catheters", Jul. 28, 2015, Precitec (Year: 2015).*

(Continued)

*Primary Examiner* — Tiffany Legette
*Assistant Examiner* — Antarius S Daniel
(74) *Attorney, Agent, or Firm* — Meunier Carlin & Curfman LLC

(57) ABSTRACT

A flow rate control device having features for selectively controlling the flow rate of a fluid over a continuous range of flow rates is provided. In particular, a flow rate control device including an inflatable flow restrictor is provided, where the flow restrictor is selectively inflatable to occlude a flow path of a fluid to thereby control the flow rate of the fluid. A flow rate control mechanism comprising a flow restrictor also is provided, the flow restrictor having an inflatable balloon for occluding a flow path of a fluid to selectively control the flow rate of the fluid.

20 Claims, 5 Drawing Sheets

(51) Int. Cl.
  *A61M 39/22* (2006.01)
  *A61M 5/14* (2006.01)

(52) U.S. Cl.
  CPC ........ *A61M 39/227* (2013.01); *A61M 39/228* (2013.01); *F16K 7/10* (2013.01); *A61M 2005/1405* (2013.01); *A61M 2205/583* (2013.01)

(58) Field of Classification Search
  CPC ............ A61M 5/16877; A61M 39/228; A61M 2039/226; A61M 5/148; A61M 5/2425; A61M 5/282; A61M 25/10181; A61M 25/10183; A61M 39/227; A61M 5/142; A61M 5/14232; A61M 5/14236; A61M 5/1424; A61M 5/145; G05D 7/005; F16K 7/10; B65D 83/0055; B65D 83/0072; A61F 11/10; A16K 7/07
  See application file for complete search history.

(56) References Cited

U.S. PATENT DOCUMENTS

| | | | |
|---|---|---|---|
| 5,080,652 A | 1/1992 | Sancoff et al. | |
| 5,105,983 A | 4/1992 | Sancoff | |
| 5,254,481 A | 10/1993 | Nishida | |
| 5,318,515 A | 6/1994 | Wilk | |
| 5,370,147 A * | 12/1994 | Brusse | F16K 7/10 137/15.11 |
| 5,538,002 A * | 7/1996 | Boussignac | A61M 16/12 128/207.14 |
| 6,234,996 B1 * | 5/2001 | Bagaoisan | A61M 5/31566 604/97.01 |
| 6,350,253 B1 | 2/2002 | Deniega et al. | |
| 6,526,977 B1 | 3/2003 | Gobel | |
| 6,802,317 B2 | 10/2004 | Gobel | |
| 6,936,035 B2 | 8/2005 | Rake et al. | |
| 6,981,967 B2 * | 1/2006 | Massengale | A61M 5/1424 604/174 |
| 7,008,403 B1 * | 3/2006 | Mallett | A61M 5/142 604/131 |
| 7,455,072 B2 | 11/2008 | Mabry et al. | |
| 8,308,688 B2 | 11/2012 | Valle et al. | |
| 8,313,687 B2 | 11/2012 | Sleva et al. | |
| 8,607,795 B2 | 12/2013 | Cuevas et al. | |
| 8,968,242 B2 | 3/2015 | Tefera et al. | |
| 2009/0118681 A1 * | 5/2009 | Molgaard-Nielsen | A61M 39/0613 604/246 |
| 2009/0217982 A1 | 9/2009 | DiPerna | |
| 2012/0103346 A1 * | 5/2012 | Keady | A61F 11/10 128/865 |
| 2012/0291540 A1 * | 11/2012 | Cooke | A61M 5/16831 73/204.11 |
| 2013/0310770 A1 | 11/2013 | Cooke et al. | |

FOREIGN PATENT DOCUMENTS

| | | |
|---|---|---|
| JP | S 6135271 U | 3/1986 |
| JP | 2012053530 A | 3/2012 |
| WO | WO-2015023036 A1 * | 2/2015 |

OTHER PUBLICATIONS

English translation of the patent document WO-2015023036-A1 (Year: 2015).*
International Search Report and Written Opinion for PCT/US2015/047145, dated Apr. 28, 2016, 13 pages.
Co-Pending U.S. Appl. No. 15/754,079, filed Feb. 21, 2018.

* cited by examiner

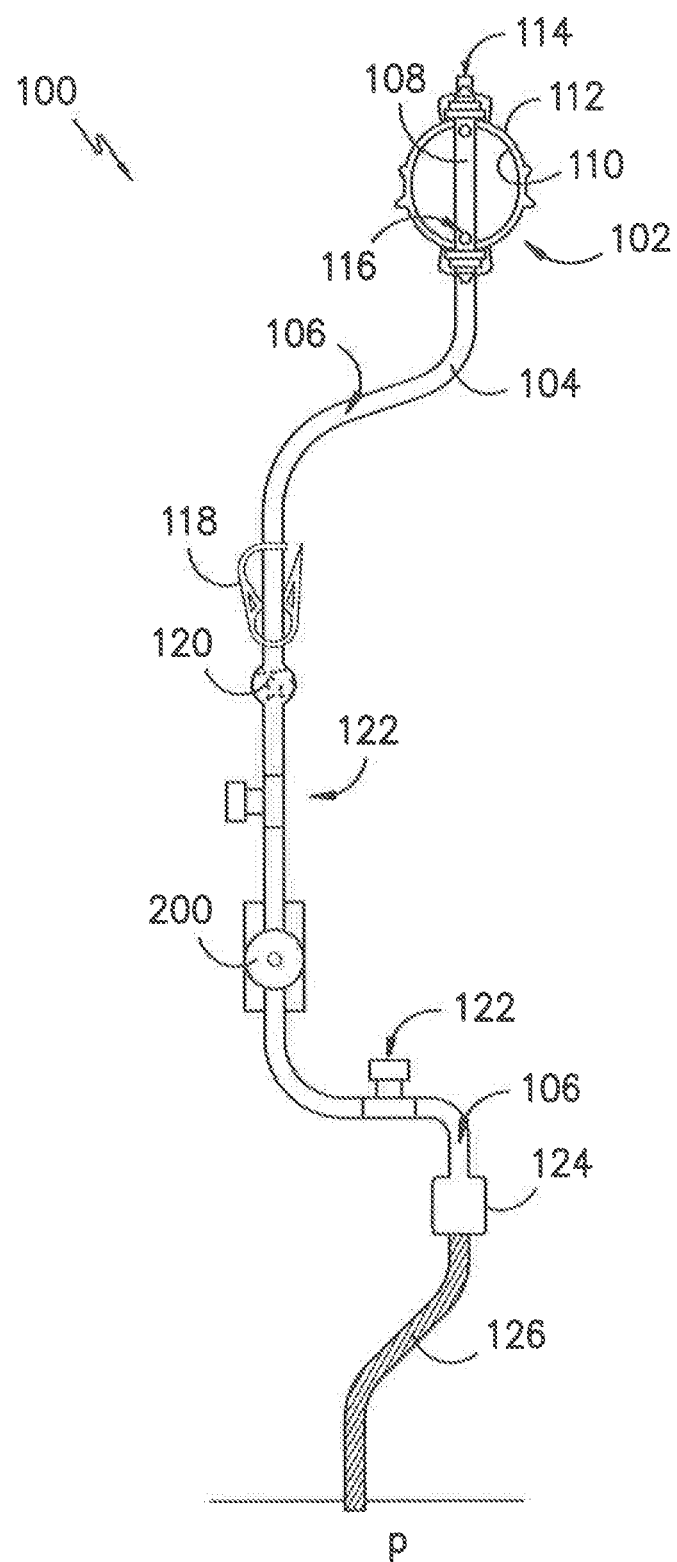
FIG. -1-

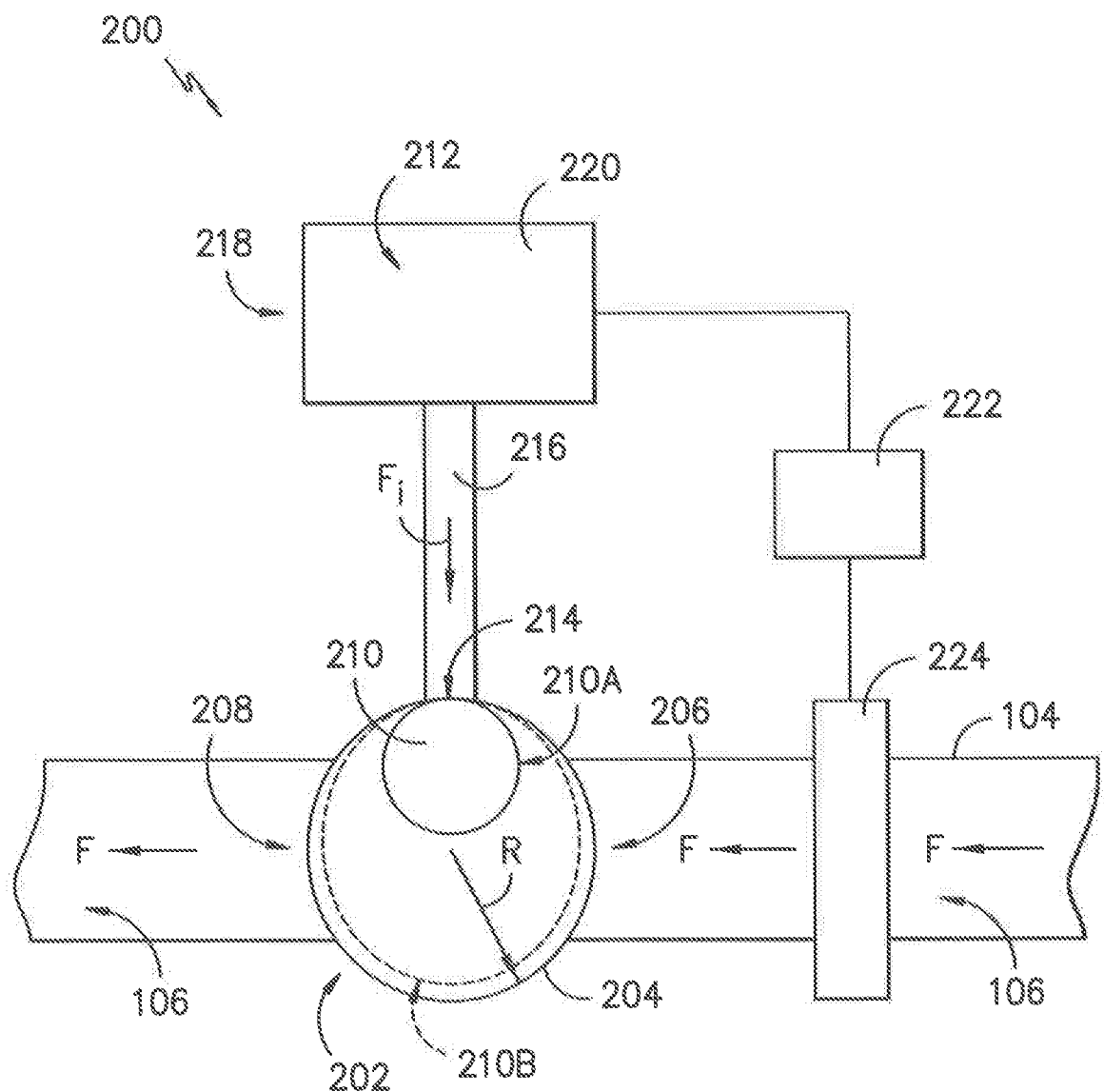
FIG. -2-

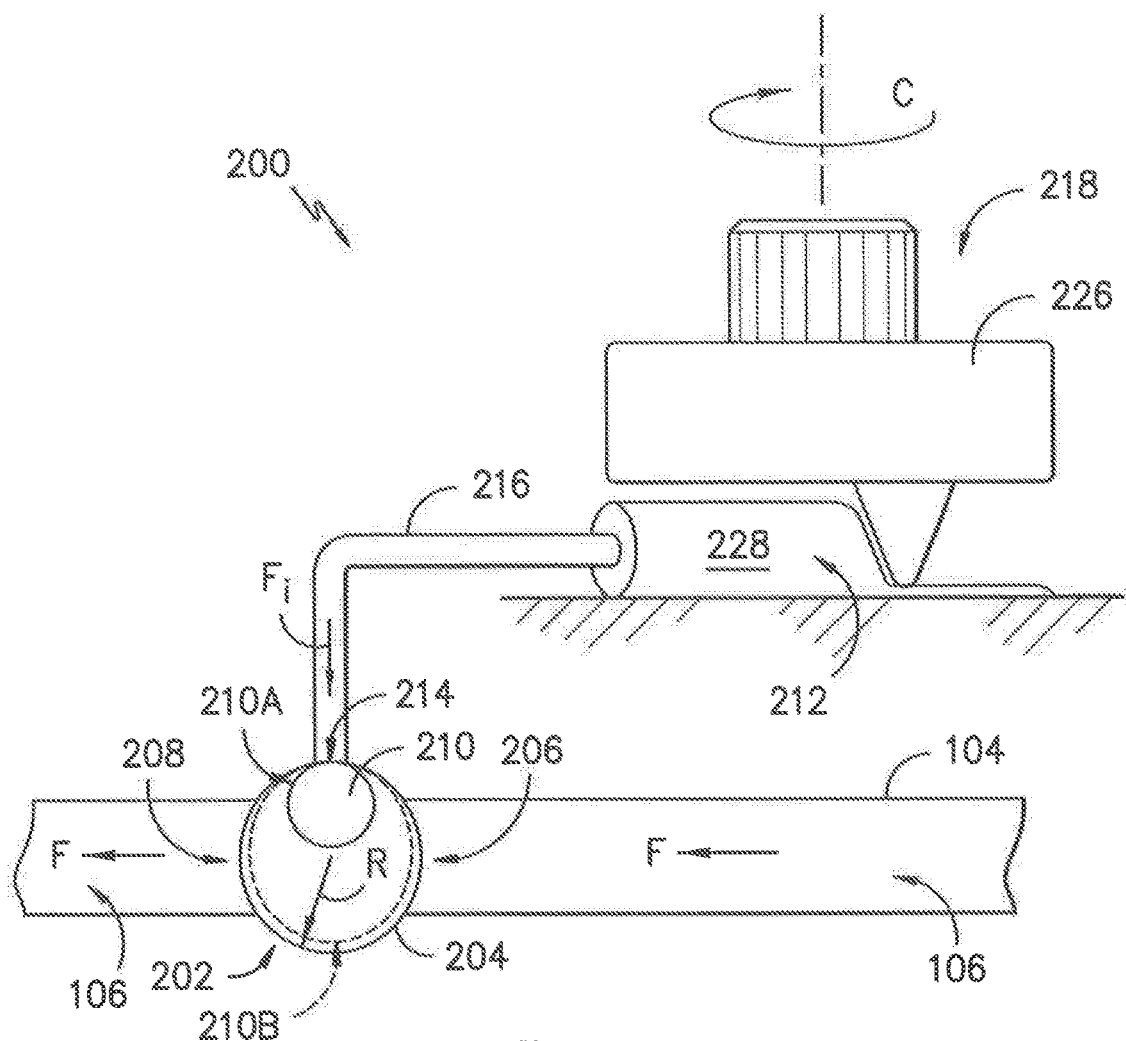
FIG. -3-
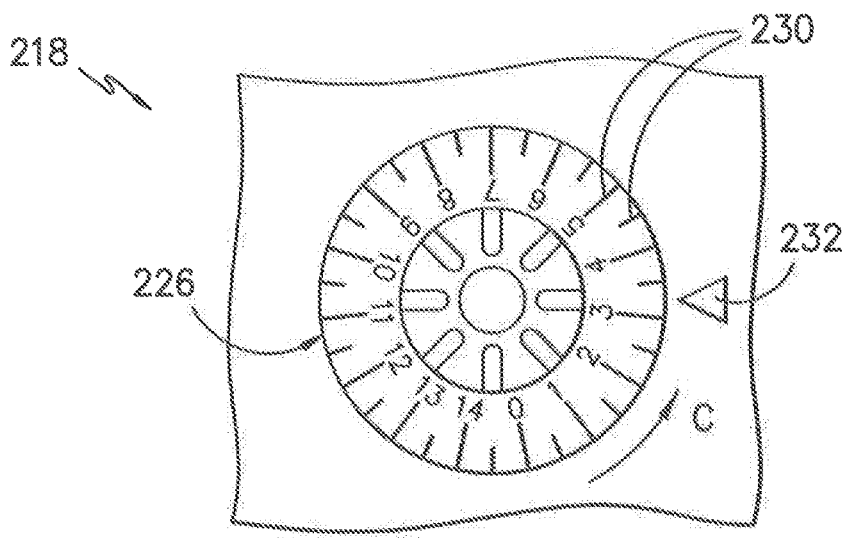
FIG. -4-

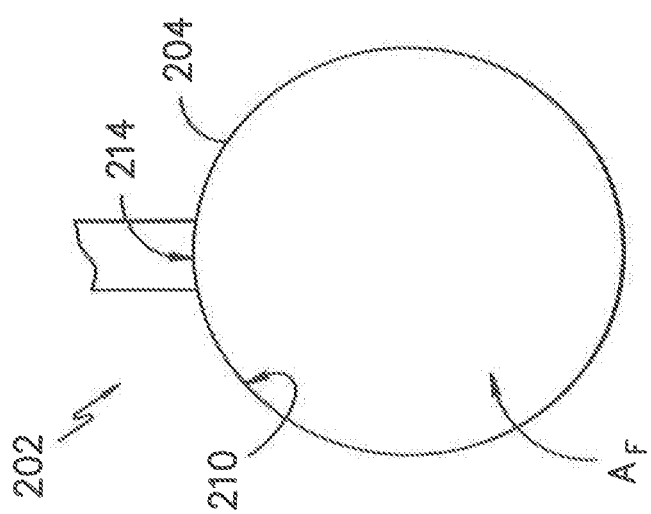
FIG. -5A-
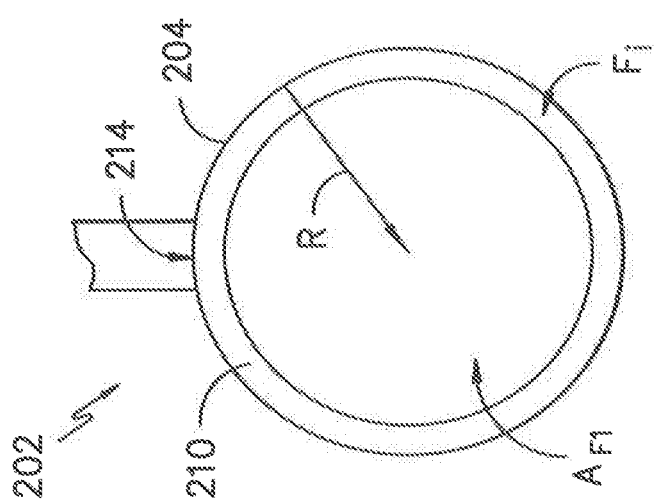
FIG. -5B-
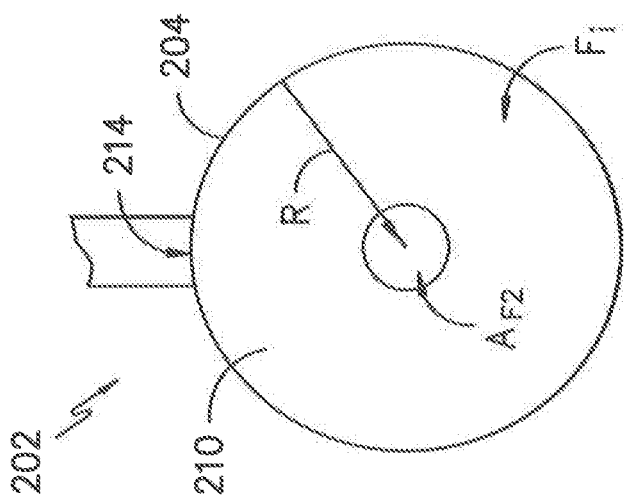
FIG. -5C-

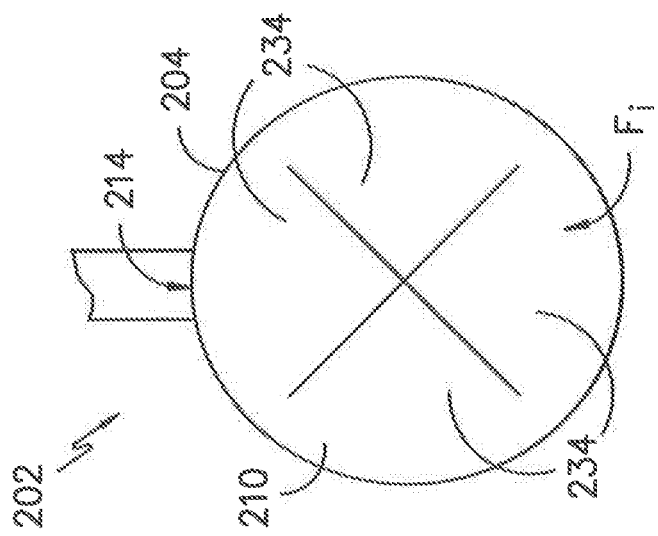
FIG. -6C-
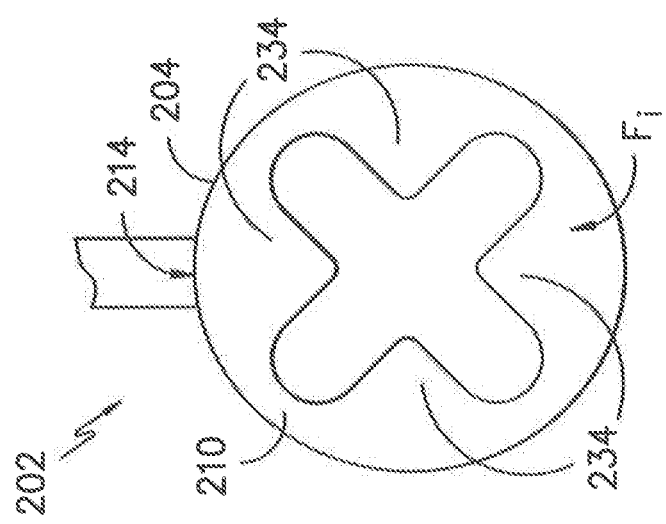
FIG. -6B-
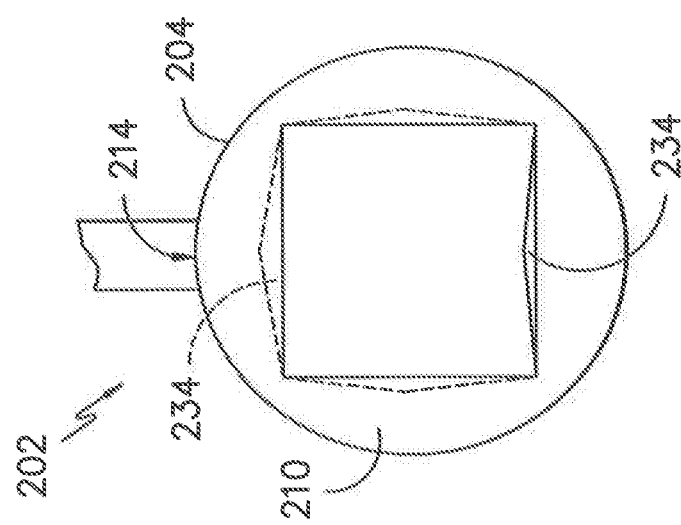
FIG. -6A-

VARIABLE FLOW RATE CONTROL DEVICE

CROSS-REFERENCE TO RELATED APPLICATIONS

This application is a national phase of and claims priority to PCT/US2015/047145, filed Aug. 27, 2015, the contents of which are incorporated herein by reference thereto.

FIELD OF THE INVENTION

The present invention relates to fluid dispensing systems and devices for regulating the flow of fluids. More particularly, the present invention relates to a flow rate control device and, most specifically, to a catheter-based system for infusing a liquid into the body of a patient at a precisely controllable flow rate.

BACKGROUND

In the medical field, therapeutic or medicinal liquids are often administered to a patient by an infusion system. There are various types of infusion systems for delivering liquids to a catheter or needle. For example, in one system the liquid is typically contained in a reservoir (a bag or a bottle) suspended above the patient and is delivered through a tube, by the force of gravity. Alternatively, the liquid may be delivered from a reservoir by an infusion pump.

It is sometimes necessary to control the flow rate at which the liquid is delivered to the patient, particularly when the liquid is to be administered continuously over an extended period of time. The flow rate may be varied depending on, for example, the specific medical treatment, type of medicinal or therapeutic agent, or the specific needs of a particular patient. Indeed, a specific patient's need or demand for a particular drug or other agent may vary over time. Moreover, often the rates of flow are relatively low, in the range of from about 0.5 to about 14 cubic centimeters of fluid per hour, and are at relatively low pressures, e.g., less than about 4 pounds per square inch (28 kilopascals).

A variety of devices and techniques have been devised to control the flow rate at which liquid is delivered. An exemplary device is described in U.S. Pat. No. 5,318,515 for an "Intravenous Flow Regulator Device and Associated Method," issued to Wilk on Jul. 7, 1994. That device has a freely accessible slider member for selecting a desired flow rate from a range of discrete flow rates. Another device is described in U.S. Pat. No. 7,455,072 for a "Device for Selectively Regulating the Flow Rate of a Fluid" to Mabry et al., issued on Nov. 25, 2004. That device has a flow rate selection mechanism that is rotatable between positions corresponding to discrete flow rates; the discrete flow rates are achieved using flow control tubes of equal cross-sectional area and different lengths. Such a device may require using the Poiseuille equation to determine the length of tubing of a given diameter required to induce a predetermined flow rate. It can be labor intensive to determine the correct length of tube to match a pump pressure output, which may vary from lot to lot of pumps. Therefore, it may be desirable to diminish the manufacturing complexity of such devices to reduce manufacturing time and expense.

In addition to reducing manufacturing complexity, more precise control of the flow rate may be desirable. For example, it may be desirable or useful to adjust the flow rate over a continuous range of flow rates rather than over a range of defined incremental or discrete flow rates. Thus, there has been a need for a device that allows the selection of any flow rate over the entire range of available flow rates while maintaining reliability of the device, particularly for devices utilizing relatively low flow rates. There has been a further need for a device in which the selected flow rate is clearly indicated to a user of the device, such as the patient and/or the caregiver. Additionally, such a device should be easy and inexpensive to manufacture so that it may be economically made as a disposable item, while providing a high degree of reliability in use.

SUMMARY

The present invention provides a flow rate control device having features for selectively controlling the flow rate of a fluid over a continuous range of flow rates. In particular, a flow rate control device including an inflatable flow restrictor is provided, where the flow restrictor is selectively inflatable to occlude a flow path of a fluid to thereby control the flow rate of the fluid. The present invention also provides a flow rate control mechanism comprising a flow restrictor having an inflatable balloon for occluding a flow path of a fluid to selectively control the flow rate of the fluid. Additional aspects and advantages of the invention will be set forth in part in the following description, may be apparent from the description, or may be learned through practice of the invention.

In a first exemplary embodiment, a flow rate control device for selectively controlling a flow rate of a fluid is provided. The flow rate control device includes a conduit providing a flow path for the fluid and an inflatable flow restrictor for occluding the flow path of the fluid. The flow restrictor has an inflatable portion in fluid communication with a source of inflation fluid for inflating the inflatable portion of the flow restrictor, a fluid inlet for ingress of the fluid to the flow restrictor, a fluid outlet for egress of the fluid from the flow restrictor, and an opening for fluid communication between the flow restrictor and the source of inflation fluid. The flow rate control device also includes an actuator for controlling a flow of inflation fluid from the source of inflation fluid to the flow restrictor. The flow restrictor is selectively inflatable to control the flow rate of the fluid over a range of flow rates.

In a second exemplary embodiment, a flow rate control device for selectively controlling a flow rate of a fluid is provided. The flow rate control device includes a conduit providing a flow path for the fluid and a flow restrictor. The flow restrictor has an inflatable balloon positioned to occlude the flow path of the fluid upon inflation, the balloon in fluid communication with a source of inflation fluid for inflating the balloon; a fluid inlet for ingress of the fluid to the flow restrictor; and a fluid outlet for egress of the fluid from the flow restrictor. The flow rate control device also includes an actuator for controlling a flow of inflation fluid from the source of inflation fluid to the balloon. The balloon is selectively inflatable to control the flow rate of the fluid over a range of flow rates.

These and other features, aspects, and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which:

FIG. 1 provides a schematic view of a device for dispensing fluid to a patient according to an exemplary embodiment of the present subject matter.

FIG. 2 provides a schematic view of a flow rate control device according to an exemplary embodiment of the present subject matter.

FIG. 3 provides a schematic view of a flow rate control device according to another exemplary embodiment of the present subject matter.

FIG. 4 provides a top view of an actuator of the exemplary flow rate control device of FIG. 3.

FIG. 5A provides a schematic view of an inflatable flow restrictor according to an exemplary embodiment of the present subject matter, where the inflatable flow restrictor is deflated.

FIG. 5B provides a schematic view of the inflatable flow restrictor of FIG. 5A, where the inflatable flow restrictor is partially inflated.

FIG. 5C provides a schematic view of the inflatable flow restrictor of FIGS. 5A and 5B, where the inflatable flow restrictor is inflated more than as shown in FIG. 5B.

FIG. 6A provides a schematic view of an inflatable flow restrictor according to another exemplary embodiment of the present subject matter, where the inflatable flow restrictor is deflated.

FIG. 6B provides a schematic view of the inflatable flow restrictor of FIG. 6A, where the inflatable flow restrictor is partially inflated.

FIG. 6C provides a schematic view of the inflatable flow restrictor of FIGS. 6A and 6B, where the inflatable flow restrictor is fully inflated.

DETAILED DESCRIPTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

Referring to FIG. 1, the present subject matter encompasses a device 100 for dispensing fluid to a patient P and controlling the flow rate of the fluid through the device. Dispensing device 100 includes a reservoir 102 that serves as a pressurized fluid source or pump that holds medicinal fluid, such as local anesthetics (referred to hereinafter as a "pump") and that is configured to provide a source of fluid under pressure. Pump 102 forces the medicinal fluid through a conduit 104. Conduit 104 forms a continuous flow path 106 for delivery into a wound site nerve bundle or the blood stream of patient P.

In some configurations, dispensing device 100 may provide for bolus delivery. In such embodiment, conduit 104 splits into continuous or primary flow path 106 and into a controlled bolus flow path (not illustrated) for delivery into a wound site nerve bundle or the blood stream of patient P. Other aspects of the bolus delivery system are described more fully herein.

Pump 102 preferably accommodates about from 100 to 500 ml of fluid under a pressure of approximately 10 to 15 psi. Pump 102 has an inner core 108 surrounded by an elastomeric chamber 110 within a housing 112. Inner core 108 preferably has an inlet port 114 to fill the pump and an outlet port 116 in fluid communication with the conduit or tubing 104. Elastomeric chamber 110 is preferably constructed from a resilient material that may comprise a variety of elastomeric compositions, well known in the art, including vulcanized synthetic polyisoprenes, natural latex, natural rubber, synthetic rubber or silicone rubber. Exemplary pumps are described in U.S. Pat. No. 5,254,481, which is hereby incorporated by reference. A variety of other conventional pumps may be used, so long as they can impart the desired pressure on the fluid. For example, the pumps described in U.S. Pat. Nos. 5,080,652 and 5,105,983, which are hereby incorporated by reference may also be used, as well as other suitable electronic or mechanical pumps offered by other manufacturers as will be understood by those of skill in the art.

Fluid is held under pressure within elastomeric chamber 110 and flows from elastomeric chamber 110 through outlet port 116 into conduit 104 at a controlled and predictable rate. Alternatively, conduit 104 may be sized to serve as a flow restrictor.

An optional clamp 118 is positioned in the flow path 106 downstream from conduit 104. Clamp 118 can compress the flow path 106 such that fluid flow from pump 102 is occluded. Such occlusion is advantageous for the transportation and preparation of fluid delivery or dispensing device 100 as described herein. An exemplary clamp 118 also is described in U.S. Pat. No. 6,350,253, which is hereby incorporated by reference. However, a variety of other conventional clamps known in the industry may be used to occlude the flow of fluid from pump 102 through the flow path 106 such as, e.g., compression clamps, C clamps, roller clamps, and the like.

An optional filter 120 downstream of clamp 118 separates the fluid from contaminates and other undesired particles that may be found within the fluid. Filter 120 also preferably eliminates air from the fluid path 106. One such filter 120 is described in U.S. Pat. No. 6,350,253, which is hereby incorporated by reference. Other suitable filters recognized in the industry may be used to capture undesired particles and/or remove air from the system.

In some embodiments, device 100 for dispensing fluid to patient P utilizes at least one flow detector assembly 122 including a flow detector to indicate a flow condition. Desirably, one flow detector assembly 122 is located above or upstream of a flow rate control device 200 and one flow detector assembly 122 is located below or downstream of flow rate control device 200, as illustrated in FIG. 1. The particular arrangement of clamp 118, filter 120, and flow rate control device 200 herein described is merely exemplary. Clamp 118 and filter 120, if present, may be arranged with respect to flow rate control device 200 and the other components of dispensing device 100 in any order as will be easily understood by those skilled in the art.

Flow detector 122 provides a signal when the flow condition of the fluid in continuous flow path 106 has changed from a predetermined flow condition. Generally speaking, the flow rate in continuous flow path 106 can be associated with a fluid flow state such as, for example, a continuous and steady flow rate. For example, flow detector 122 may be configured to provide a signal that the flow rate of the fluid in continuous flow path 106 is less than the predetermined flow rate, within a range of predetermined flow rates, or greater than a predetermined flow rate.

As further illustrated in FIG. 1, conduit 104 may include an outlet or connection 124. Outlet 124 connects continuous flow path 106 to a catheter 126. Catheter 126 delivers the fluid into a wound site nerve bundle or the blood stream of patient P. The flow rate of fluid to patient P may be selected and controlled as further described herein.

As previously stated, some embodiments of device 100 may incorporate a bolus delivery system, such as described in U.S. Patent Application Nos. 2012/0291540 and 2013/0310770. In an exemplary embodiment, the bolus delivery system accumulates a large quantity of fluid from the bolus flow path leading from reservoir 102 and holds the fluid under pressure until the bolus dose is triggered by a patient operable actuator for release into patient P. Such a large volume bolus delivery system is configured to receive fluid, elastically expand to pressurize fluid, store the pressurized fluid, and dispense the pressurized fluid, while avoiding bolus refill during bolus delivery or after bolus delivery but before it is enabled to elastically expand in a subsequent delivery cycle. The actuator is configured such that it does not require effort to force the fluid out of the bolus reservoir and such that when actuated by the patient, fluid is permitted to flow out of the bolus reservoir to the patient without further action by the patient. The large volume bolus delivery system is desirably a PCA device as described at, for example, U.S. Pat. No. 6,936,035 for "Patient Controlled Drug Administration Device" issued Aug. 30, 2005 to Rake et al. and U.S. Pat. No. 8,308,688 for "Large-Volume Bolus Patient Controlled Drug Administration Device" issued Nov. 13, 2012 to Valle et al., the contents of each being incorporated herein by reference.

Downstream from the large volume bolus delivery system, continuous flow path 106 and the bolus dose flow path converge into a single flow path to patient P. An optional clamp and an optional filter may be positioned in the bolus flow path downstream from conduit 104. The clamp can compress the bolus flow path such that fluid flow from pump 102 is occluded. Such occlusion is advantageous for the transportation and preparation of fluid delivery device 100 as described herein.

The release-rate of the bolus dose to patient P is controlled by the decompression of the elastomeric bolus reservoir, by the pressure gradient at the actuator, and the diameter of the catheter 126. Advantageously, patient P does not have to provide pressure to force fluid out of the large volume bolus delivery system into the narrower bolus flow path. Rather, patient P can turn the stopcock or release the push button to administer the bolus dose. If patient P activates the bolus actuator or valve prior to the time the bolus reservoir has filled to its capacity, patient P receives less than the full amount of the bolus dose. In effect, this prevents the patient from self-administering more than the maximum desired amount of fluid per the time specified as a large volume bolus dose.

A flow detector assembly 122 with its flow detector may be located downstream of the location where continuous flow path 106 and the bolus dose flow path converge into a single flow path. In this location, the flow detector 122 provides a signal that the flow rate of the fluid in the single flow path is less than a predetermined flow rate; such a signal indicates a flow state that is less than a continuous and substantially constant flow rate of fluid.

Referring now to FIG. 2, flow rate control device 200 may be described in greater detail. Flow rate control device 200 sets the continuous and substantially constant flow rate of fluid from pump 102 to patient P via conduit 104. More particularly, flow rate control device 200 provides selective control of the flow rate of fluid F through conduit 104. The flow rate may be adjusted to a rate within a range of from about 0.5 to about 14 cubic centimeters of fluid per hour. Desirably, the flow rate may be from about 0.5 to about 7 or from about 1 to about 12 cubic centimeters per hour. Flow rate control device 200 may be manually adjustable or may be automatically adjusted by a controller assembly or the like, as further described below.

In the exemplary embodiment shown in FIG. 2, flow rate control device 200 includes an inflatable flow restrictor 202 for occluding the flow path of fluid F to control the flow rate of the fluid. Flow restrictor 202 includes a housing 204 defining a fluid inlet 206 and a fluid outlet 208. Fluid inlet 206 permits ingress of a flow of fluid F from conduit 104 into housing 204, and fluid outlet 208 permits egress of the flow of fluid F from housing 204 into conduit 104. Fluid F received at fluid inlet 206 of flow restrictor 202 is at a relatively constant pressure, i.e., flow restrictor 202 is operated at relatively constant inlet pressures. Typical pressure profiles of the fluid encountered by flow restrictor 202 during its operation generally are as described at, e.g., U.S. Pat. No. 8,968,242 for "Inflatable Elastomeric Pump for an Infusion Assembly," issued Mar. 3, 2015 to Tefer, et al., the contents of which is incorporated herein by reference. Tefer, et al. illustrates pressure profiles of the fluid environment downstream of an elastomeric pump, which would be typical of the operating pressure profiles experienced by flow restrictor 202.

Flow restrictor 202 further includes an inflatable portion 210 that is in fluid communication with a source 212 of inflation fluid $F_i$ for inflating the inflatable portion 210 of flow restrictor 202. Source 212 generally may be a volume that contracts to inflate flow restrictor 202, i.e., by expelling inflation fluid $F_i$ to inflatable portion 210, and expands to deflate flow restrictor 202, or expands when flow restrictor 202 is deflated, i.e., by receiving inflation fluid $F_i$ from inflatable portion 210. In various embodiments, source 212 may be, e.g., a piston, syringe, diaphragm, or the like.

Housing 204 of flow restrictor 202 defines an opening 214 to provide fluid communication between flow restrictor 202 and source 212 of inflation fluid—more specifically, between inflatable portion 210 and source 212 of inflation fluid through an inflation fluid flow path 216. Inflatable portion 210 is configured such that, when inflatable portion 210 is deflated, flow through flow restrictor 202 is unimpeded. That is, inflatable portion 210 does not occlude flow of fluid F through flow restrictor 202 when inflatable portion 210 is not inflated.

However, inflatable portion 210 may be selectively inflated to occlude the flow of fluid F through flow restrictor 202. Inflatable portion 210 may be partially inflated to control the flow rate of fluid F over a range of flow rates. In particular, the degree of inflation of inflatable portion 210, which depends on the amount of inflation fluid from source 212 provided to inflatable portion 210, determines the flow rate through flow restrictor 202. The more or greater inflatable portion 210 is inflated, the more flow path 106 of fluid F is occluded and the lower the flow rate of fluid F is downstream of flow restrictor 202. As illustrated in FIGS. 2 and 3, in some embodiments, inflatable portion 210 may be generally spherical in shape upon inflation. In particular, as inflation fluid $F_i$ is provided to it, inflatable portion 210 may increase in size radially outwardly, e.g., from a first size 210A corresponding to a first radius of the spherical shape of inflatable portion 210 to a second size 210B corresponding to a second radius of the spherical shape of inflatable portion 210. However, it should be readily understood that the first and second sizes of inflatable portion 210 illustrated in FIGS. 2 and 3 are by way of example only and that inflatable portion 210 may have any size over a range of radii from zero to a maximum radius permitted by housing 204. The radius of inflatable portion 210, and thereby its size, may vary based on the selected flow rate of fluid F, where the radial size of inflatable portion 210 is inversely proportional to the flow rate of fluid F. Moreover, as described below, inflatable portion 210 may have other shapes and configurations as well.

In some embodiments, inflatable portion 210 is made from an elastic material such that inflatable portion 210 expands when inflated with inflation fluid from source 212 to store inflation fluid $F_i$ under pressure. When deflation is desired, e.g., to alter the flow rate of fluid F, flow restrictor 202 expels the inflation fluid $F_i$ within inflatable portion 210 from flow restrictor 202 to source 212 of inflation fluid. In other embodiments, inflatable portion 210 is made from a non-elastic material that expands upon receipt of inflation fluid $F_i$ to inflate flow restrictor 202 and contracts as inflation fluid $F_i$ is expelled to deflate flow restrictor 202. As will be understood by those of ordinary skill in the art, inflatable portion 210 also may be made from other materials.

Inflation fluid $F_i$ from source 212 of inflation fluid may be provided to flow restrictor 202 by a variety of means. As illustrated in FIG. 2, in one embodiment, flow rate control device 200 may utilize an automatic actuator 218 to control a flow of inflation fluid $F_i$ from source 212 to flow restrictor 202. More particularly, actuator 218 may be an electromechanical pump 220 controlled by a control assembly 222. For example, a flow sensor 224 may be positioned within the flow path 106 of fluid F upstream of flow restrictor 202. Flow sensor 224 determines the flow rate of fluid F, and control assembly 222 determines whether the flow rate of fluid F needs to be adjusted, e.g., based on a predetermined flow rate for the delivery of fluid F to the patient P. If the flow rate should be lowered, control assembly 222 communicates to pump 220 to lower the flow rate of fluid F, e.g., by providing inflation fluid $F_i$ to inflatable portion 210 of flow restrictor 202 through inflation fluid flow path 216. The inflation fluid inflates flow restrictor 202 and thereby occludes the flow of fluid F, which lowers the flow rate of the fluid through flow restrictor 202 and within flow path 106 downstream of flow restrictor 202. The amount of inflation fluid $F_i$ provided to inflatable portion 210 is determined based on the desired flow rate of fluid F downstream of flow restrictor 202. In this way, using actuator 218, flow restrictor 202 is selectively inflatable to control the flow rate of fluid F over a range of flow rates.

Referring now to FIG. 3, in another embodiment, flow rate control device 200 may utilize a manual actuator 218 to control a flow of inflation fluid $F_i$ from source 212 to flow restrictor 202. More particularly, actuator 218 may be a rotatable dial 226 operable by a user of flow rate control device 200 to select a flow rate of the fluid F. Further, source 212 of inflation fluid $F_i$ may include a reservoir 228 configured such that rotating the dial in a circumferential direction C compresses reservoir 228 to expel inflation fluid $F_i$ from the reservoir. The expelled inflation fluid flows to inflatable portion 210 of flow restrictor 202 to inflate flow restrictor 202. In this way, using actuator 218, flow restrictor 202 is selectively inflatable to control the flow rate of fluid F over a range of flow rates.

As shown in FIG. 4, in some embodiments of manual actuator 218, the dial may comprise indicia 230 for indicating to the user the selected flow rate of fluid F. Indicia 230 may comprise a series of numbers representing the range of flow rates selectable using flow rate control device 200. The numbers are arranged sequentially about the dial along the circumferential direction C, and an indicator 232 is provided on flow rate control device 200 such that when the dial is rotated, the portion of indicia 230 adjacent indicator 232 indicates the current or selected flow rate to the user. In other embodiments, indicia 230 may be any means for indicating the selected flow rate to a user and/or may be provided on any appropriate feature or component of flow rate control device 200.

FIGS. 5A-5C provide schematic views of an alternative exemplary embodiment of flow restrictor 202. More specifically, FIGS. 5A, 5B, and 5C illustrate flow restrictor 202 according to an exemplary embodiment in which inflatable portion 210 inflates radially inward as inflation fluid $F_i$ is provided to flow restrictor 202. By inflating radially inward along a radial direction R, inflatable portion has a generally toroidal or donut shape upon inflation. Further, as inflation fluid $F_i$ is provided to flow restrictor 202 to inflate inflatable portion 210 and inflatable portion 210 expands inwardly along the radial direction R, the cross-sectional area of the flow path 106 of fluid F through flow restrictor 202 decreases. For example, when flow restrictor 202 is deflated as shown in FIG. 5A, the cross-sectional area $A_F$ of flow path 106 within flow restrictor 202 is at a maximum. As inflatable portion 210 is inflated with inflation fluid $F_i$, the cross-sectional area $A_F$ decreases, e.g., to a first cross-sectional area $A_{F1}$ as shown in FIG. 5B and then, as additional inflation fluid $F_i$ is provided to inflatable portion 210, to a second cross-sectional area $A_{F2}$ as shown in FIG. 5C. Of course, inflatable portion 210 may be inflated such that cross-sectional area $F_A$ has other values or sizes as well. As a result of the decreasing cross-sectional area $A_F$, the flow rate of fluid F through flow restrictor 202 decreases as inflatable portion 210 is inflated.

FIGS. 6A-6C provide schematic views of an alternative exemplary embodiment of flow restrictor 202. More particularly, FIGS. 6A, 6B, and 6C illustrate flow restrictor 202 according to an exemplary embodiment in which inflatable portion 210 comprises a plurality of inflatable arms 234. As shown in FIG. 6A, arms 234 open freely when deflated to allow the fluid F to freely flow through flow restrictor 202, i.e., the flow rate of fluid F through flow restrictor 202 is at a maximum when flow restrictor 202 is deflated. As shown in FIGS. 6B and 6C, arms 234 of inflatable portion 210 stiffen upon inflation to occlude flow of fluid F through flow restrictor 202. FIG. 6B illustrates an intermediate position in which inflatable portion 210 is partially inflated such that arms 234 partially protrude within the flow path 106 of the fluid F. The protruding arms 234 occlude the flow of fluid F such that the flow rate of fluid F through flow restrictor 202 is lower for the configuration shown in FIG. 6B than the configuration shown in FIG. 6A. When fully inflated, as illustrated in FIG. 6C, arms 234 meet to fully occlude the flow of fluid F through flow restrictor 202.

The embodiments of flow restrictor 202 illustrated in FIGS. 2, 3, 5A-5C, and 6A-6C are provided by way of example only. Flow restrictor 202 and inflatable portion 210 also may have other shapes, sizes, and configurations for restricting the flow of fluid through flow restrictor 202 to selectively control the flow rate of fluid within a device such as dispensing device 100.

In some embodiments, inflatable portion 210 of flow rate control device 200 may be a balloon that occludes the flow path of fluid F upon inflation to control the flow rate of fluid F, but inflatable portion 210 may have any appropriate configuration or construction. In embodiments in which inflatable portion 210 is an inflatable balloon, flow restrictor 202 may include a housing 204 defining a fluid inlet 206 for ingress of fluid F from conduit 104 and a fluid outlet 208 for egress of fluid F to conduit 104. Flow restrictor 202 further may include a balloon 210 that is in fluid communication with a source 212 of inflation fluid $F_i$ for inflating the balloon. Housing 204 of flow restrictor 202 defines an opening 214 to provide fluid communication between the balloon and the source of inflation fluid through an inflation fluid flow path 216. The balloon is configured such that, when deflated, flow through flow restrictor 202 is unimpeded and, when inflated, the balloon occludes the flow of fluid F through flow restrictor 202 to lower the flow rate of fluid F. The balloon is selectively inflatable to control the flow rate of fluid F.

Further, in embodiments in which inflatable portion 210 is an inflatable balloon, the balloon is desirably made from a pliable polymer such as polyethylene terephthalate (PET), polyvinyl chloride (PVC), polyurethane (PU), polyolefins like polyethylene and polypropylene, and/or blends or mixtures thereof. It should be very thin; on the order of about 25 microns or less, e.g., 20 microns, 15 microns, 10 microns, or even as low as 5 microns in thickness but at least one micron in thickness. In some embodiments employing a balloon as inflatable portion 210, the balloon may be a low pressure balloon operating at about 30 mmH$_2$O or less, such as 25 mmH$_2$O, 20 mmH$_2$O, 15 mmH$_2$O, or less, desirably between about 15 to 25 mmH$_2$O. Such a balloon is described in U.S. Pat. Nos. 6,802,317 and 6,526,977 to Gobel, which describe a cuff for obturating a patient's trachea as hermetically as possible and are incorporated herein by reference.

In alternative embodiments, the balloon may be formed from thermoplastic polyurethane polymers, thermoplastic polyolefin elastomers, thermoplastic polyolefin block copolymers, SBS di-block elastomers, SEBS tri-block elastomers, polyvinyl chloride, polyethylene terephthalate, and blends and mixtures thereof. Such balloons are described in, e.g., U.S. Pat. No. 8,607,795 to Cuevas, et al. Further, polyurethane may be used, and useful polyurethanes include those from the Dow Chemical Company (Dow Plastics) available under the tradename Pellethane®. Pellethane® thermoplastic polyurethane elastomer is available in a number of grades and hardnesses and the particular one selected for a specific use will depend on the properties desired in the final product. The hardness of a polymer, for example, is an attribute that may be varied to meet the requirements of various applications. One exemplary polyurethane is designated Pellethane® 2363-90 A and has a durometer hardness of 90 A (ASTM D-2240). This polyurethane has a softening temperature of 110° C. (ASTM D-790) and a melt index of 30 g/10 min. at 224° C., 2160 g (ASTM D-1238). As stated, the balloon is desirably very thin, with a thickness on the order of about 25 microns or less. Such balloons are described in, e.g., U.S. Pat. No. 8,313,687 to Sleva, et al.

In some embodiments, the balloon is configured to inflate radially outwardly with respect to the flow path 106, e.g., along radial direction R, such that the balloon has a generally spherical shape upon inflation, similar to the inflatable portion 210 illustrated in FIGS. 2 and 3. In other embodiments, the balloon is configured to inflate radially inward with respect to the flow path 106, e.g., along a radial direction R, such that the balloon has a generally toroidal shape upon inflation, like inflatable portion 210 as illustrated in FIGS. 5A, 5B, and 5C. In still other embodiments, the balloon is configured to have a plurality of inflatable arms that open freely when deflated to allow the fluid to freely flow through flow restrictor 202 and that stiffen upon inflation to occlude flow of the fluid F through flow restrictor 202, similar to inflatable portion 210 shown in FIGS. 6A, 6B, and 6C.

This written description uses examples to disclose the invention, including the best mode, and also to enable any person skilled in the art to practice the invention, including making and using any devices or systems and performing any incorporated methods. The patentable scope of the invention is defined by the claims and may include other examples that occur to those skilled in the art. Such other examples are intended to be within the scope of the claims if they include structural elements that do not differ from the literal language of the claims or if they include equivalent structural elements with insubstantial differences from the literal language of the claims.

We claim:

1. A flow rate control device for selectively controlling a flow rate of a medicinal fluid from a medicinal fluid pump to a patient, the flow rate control device comprising:
   a conduit providing a flow path for the medicinal fluid;
   an inflatable flow restrictor for occluding the flow path of the medicinal fluid, the flow restrictor including:
      an inflatable portion in fluid communication with a reservoir of an inflation fluid for inflating the inflatable portion of the flow restrictor, and
      a housing defining:
         a spherically shaped inner surface,
         a fluid inlet for ingress of the medicinal fluid to the flow restrictor,
         a fluid outlet for egress of the medicinal fluid from the flow restrictor, and
         an opening for fluid communication between the flow restrictor and the reservoir of the inflation fluid;
   an actuator for controlling a flow of the inflation fluid from the reservoir of the inflation fluid to the flow restrictor, the actuator comprising a rotatable dial such that rotating the dial causes a projection extending from a bottom surface of the dial to compress the reservoir and expel the inflation fluid from the reservoir to the inflatable portion of the flow restrictor thereby inflating the flow restrictor, where the axis of rotation of the dial is transverse to a direction of flow of the inflation fluid within the reservoir,
   wherein the inflatable portion of the flow restrictor is disposed in the housing and selectively inflates and deflates within the housing over a range of radii to control the flow rate of the medicinal fluid over a range of flow rates, and
   wherein an outer surface of the inflatable portion contacts at least a portion of the spherically shaped inner surface of the housing opposite the opening upon inflation.

2. The flow rate control device of claim 1, wherein the inflatable portion has a generally spherical shape upon inflation corresponding to the inner surface of the housing.

3. The flow rate control device of claim 1, wherein the inflatable portion inflates radially inward with respect to the flow path such that the inflatable portion has a generally toroidal shape upon inflation.

4. The flow rate control device of claim 1, wherein the inflatable portion comprises a plurality of inflatable arms that open freely when deflated to allow the medicinal fluid to freely flow through the flow restrictor and that stiffen upon inflation to occlude flow of the medicinal fluid through the flow restrictor.

5. The flow rate control device of claim 1, wherein the housing limits a maximum inflated size of the inflatable portion.

6. The flow rate control device of claim 1, wherein the housing defines an inner cavity having a generally spherical shape, the generally spherical shape having a larger diameter than that of the fluid inlet, the inflatable portion inflating within the inner cavity.

7. The flow rate control device of claim 6, wherein the inflatable portion inflates radially inward with respect to the flow path such that the inflatable portion has a generally toroidal shape upon inflation.

8. A flow rate control device for selectively controlling a flow rate of a medicinal fluid, the flow rate control device comprising:
   a conduit providing a flow path for the medicinal fluid;
   a flow restrictor disposed in the conduit, the flow restrictor including
      an inflatable balloon positioned to occlude the flow path of the medicinal fluid upon inflation, the balloon in fluid communication with a reservoir of an inflation fluid for inflating the balloon, and
      a housing defining a fluid inlet for ingress of the medicinal fluid from the conduit to the flow restrictor, a fluid outlet for egress of the medicinal fluid from the flow restrictor to the conduit, and an inner cavity having a generally spherical shape, the generally spherical shape having a larger diameter than that of the fluid inlet, the inflatable balloon inflating within the inner cavity; and
      an actuator for controlling a flow of the inflation fluid from the reservoir of the inflation fluid to the balloon,
   wherein the balloon inflates radially inward with respect to the flow path,
   wherein the balloon is selectively inflatable to control the flow rate of the medicinal fluid over a range of flow rates,
   wherein the balloon comprises a plurality of inflatable arms that open freely when deflated to allow the medicinal fluid to freely flow through the flow restrictor and that stiffen upon inflation to occlude flow of the medicinal fluid through the flow restrictor, each of the plurality of inflatable arms defining a generally triangular shape when inflated, each of the plurality of inflatable arms is spaced 45 degrees from each other,
   wherein the reservoir contracts to inflate the balloon,
   wherein the actuator comprises a rotatable dial and rotating the dial causes a projection extending from a bottom surface of the dial to compress the reservoir to expel the inflation fluid from the reservoir to the inflatable balloon of the flow restrictor thereby inflating the flow restrictor, where the axis of rotation of the dial is transverse to a direction of flow of the inflation fluid in the reservoir.

9. The flow rate control device of claim 8, wherein the balloon has a thickness of less than about 25 microns.

10. The flow rate control device of claim 8, wherein the balloon is made from a polyurethane.

11. The flow rate control device of claim 8, wherein each of the plurality of inflatable arms as a generally triangular shaped with a decreasing taper extending towards a longitudinal axis of the balloon.

12. The flow rate control device of claim 8, wherein the projection extending from the bottom surface of the actuator extends in the same direction as an axis of rotation of the dial.

13. The flow rate control device of claim 12, wherein as the dial is rotated in a circumferential direction, the projection moves along a length of the reservoir transverse to the axis of rotation of the dial thereby compressing the reservoir to expel the inflation fluid from the reservoir.

14. The flow rate control device of claim 8, wherein the dial comprises indicia for indicating a selected flow rate to the user.

15. The flow rate control device of claim 8, wherein the range of flow rates is from 0.5 to 14 cubic centimeters of fluid per hour.

16. The flow rate control device of claim 8, wherein the inflatable arms seal against each other when fully inflated occluding flow of medicinal fluid through the flow restrictor.

17. The flow rate control device of claim 8, wherein the plurality of inflatable arms includes four inflatable arms.

18. A flow rate control device for selectively controlling a flow rate of a medicinal fluid from a medicinal fluid pump to a patient, the flow rate control device comprising:
   a conduit providing a flow path for the medicinal fluid;
   an inflatable flow restrictor for occluding the flow path of the medicinal fluid, the flow restrictor including:
      an inflatable portion in fluid communication with a source of an inflation fluid for inflating the inflatable portion of the flow restrictor, the source of the inflation fluid comprising a reservoir, and
      a housing defining:
         a fluid inlet for ingress of the medicinal fluid to the flow restrictor,
         a fluid outlet for egress of the medicinal fluid from the flow restrictor, and
         an opening for fluid communication between the flow restrictor and the reservoir of the inflation fluid; and
      an actuator for controlling a flow of the inflation fluid from the reservoir of the inflation fluid to the flow restrictor, the actuator comprising a rotatable dial including indicia for indicating a selected flow rate of the medicinal fluid to a user,
   wherein rotating the dial causes a projection extending from a bottom surface of the dial to compress the reservoir and expel the inflation fluid from the reservoir to the inflatable portion of the flow restrictor thereby inflating the flow restrictor, where the axis of rotation of the dial is transverse to a direction of flow of the inflation fluid within the reservoir,
   wherein the inflatable portion of the flow restrictor is disposed in the housing and inflates within the housing,
   wherein the inflatable portion comprises a plurality of inflatable arms that open freely when deflated to allow the medicinal fluid to freely flow through the flow restrictor and that stiffen upon inflation to occlude flow of the medicinal fluid through the flow restrictor, each of the plurality of inflatable arms defining a triangular shape when inflated,
   wherein the flow restrictor is selectively inflatable to control the flow rate of the medicinal fluid over a range of flow rates,
   wherein the indicia comprise a series of numbers representing the range of flow rates selectable using the flow rate control device, and
   wherein each of the plurality of inflatable arms is spaced 45 degrees from each other.

19. The flow rate control device of claim 18, wherein the housing defines an inner cavity having a generally spherical shape, the generally spherical shape having a larger diameter than that of the fluid inlet, the inflatable portion inflating within the inner cavity.

20. The flow rate control device of claim 18, wherein each of the plurality of inflatable arms has a generally triangular shaped with a decreasing taper extending towards a longitudinal axis of the balloon,
 wherein the inflatable arms seal against each other when fully inflated occluding flow of medicinal fluid through the flow restrictor
 wherein the plurality of inflatable arms includes four inflatable arms.

* * * * *